(12) United States Patent
Feucht et al.

(10) Patent No.: US 6,365,550 B1
(45) Date of Patent: Apr. 2, 2002

(54) FLUFENACET-BASED HERBICIDAL COMPOSITIONS

(75) Inventors: Dieter Feucht, Monheim; Mark-Wilhelm Drewes, Langenfeld; Peter Dahmen, Neuss; Rolf Pontzen, Leichlingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/619,997

(22) Filed: Jul. 20, 2000

(30) Foreign Application Priority Data

Jul. 27, 1999 (DE) ......................... 199 35 215

(51) Int. Cl.$^7$ ............................................... A01N 57/00
(52) U.S. Cl. ..................................... 504/128
(58) Field of Search ......................... 504/128

(56) References Cited

U.S. PATENT DOCUMENTS

| | | | |
|---|---|---|---|
| 3,799,758 A | 3/1974 | Franz | 71/86 |
| 3,977,860 A | 8/1976 | Franz | 71/86 |
| 4,168,963 A | 9/1979 | Rupp et al. | 71/86 |
| 4,384,880 A | 5/1983 | Large | 71/87 |
| 4,405,531 A | 9/1983 | Franz | 260/501.12 |
| 4,659,860 A | 4/1987 | Franz | 558/231 |
| 4,840,659 A | 6/1989 | Franz | 71/86 |

FOREIGN PATENT DOCUMENTS

| | | |
|---|---|---|
| WO | WO 00/08934 | 2/2000 |
| WO | WO 00/08935 | 2/2000 |

OTHER PUBLICATIONS

Weeds, S.R. Colby, (month unavailable) 1967, pp. 20–22, Calculating Synergistic and Antagonistic Responses of Herbicide Combinations.

Primary Examiner—José G. Dees
Assistant Examiner—Alton Pryor
(74) Attorney, Agent, or Firm—Joseph C. Gil

(57) ABSTRACT

The invention relates to synergistic herbicidal compositions comprising a combination of (a) flufenacet (N-(4-fluoro-phenyl)-N-(i-propyl)-2-(5-trifluoromethyl-1,3,4-thiadiazol-2-yl-oxy)-acetamide), of the formula (I),

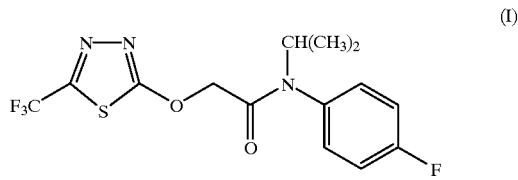

(I)

and (b) glyphosate (N-phosphonomethyl-glycine) or its esters which are described in the description and/or salts of glyphosate and its esters which are formed with basic compounds and/or (c) glufosinate (2-amino-4-(hydroxy-methyl-phosphinyl)-butanoic acid) and/or the salts of glufosinate which are formed with basic compounds, where 0.01 to 100 parts by weight of glyphosate and/or its salts or its esters and/or their salts, or of glufosinate and/or its salts, are used per part by weight of flufenacet.

9 Claims, No Drawings

FLUFENACET-BASED HERBICIDAL COMPOSITIONS

The invention relates to new herbicidal synergistic active compound combinations which are composed on the one hand of the known active compound flufenacet (N-(4-fluoro-phenyl)-N-(i-propyl)-2-(5-trifluoromethyl-1,3,4-thiadiazol-2-yl-oxy)-acetamide) and, on the other hand, of the known active compound glyphosate (M-phosphonomethyl-glycine) and/or the derivatives and salts of glyphosate, or, on the one hand, of the known active compound flufenacet and, on the other hand, of the known active compound glufosinate (2-amino-4-(hydroxy-methylphosphinyl)-butanoic acid) and/or the derivatives and salts of glufosinate, and which can be used particularly successfully for controlling weeds.

The active compound flufenacet has already been known for several years (cf. EP-A-348737/U.S. Pat. No 4,968,342). The possibility of using flufenacet in combinations with selective herbicides and/or with safeners for the selective control of weeds in various crops such as, for example, in maize or wheat, is already known, too (cf. U.S. Pat. Nos. 5,593,942, 5,858,920). In the case of flufenacet, the optimal period of application is before emergence of the harmful plants to be controlled. The use of flufenacet in combination with unselective herbicides, which are generally applied after the plants have emerged, was hitherto unknown.

The active compound glyphosate and its derivatives and salts have also been known for a long time as agents for controlling weeds (cf. DE-A-2 152 826/DE-A2 167 05/U.S. Pat. Nos. 3,799,758/3,977,860/4,405,531/EP-A-54 382). However, this active compound and its derivatives and salts only act when applied after the weeds have emerged; there is virtually no action against weeds which emerge for the first time after the application.

The active compound glufosinate and its derivatives and salts have also been known for a long time as agents for controlling weeds (cf. DE-A-2 717 440/U.S. Pat. No. 4,168, 963). Again, however, this active compound and its derivatives and salts only act when applied after the weeds have emerged; again, there is virtually no action against weeds which emerge for the first time after the application.

Surprisingly, it has now been found that the active compound flufenacet, when applied jointly with the known active compound glyphosate and/or its derivatives and salts, or when applied jointly with the known active compound glufosinate and/or its derivatives and salts, shows pronounced synergistic effects as regards the herbicidal action and can be used particularly advantageously in broad-spectrum combination products for controlling weeds.

The invention relates to synergistic herbicidal compositions comprising a combination of
(a) flufenacet (N-(4-fluoro-phenyl)-N-(i-propyl)-2-(5-trifluoromethyl-1,3,4-thiadiazol-2-yl-oxy)-acetamide), of the formula (I),

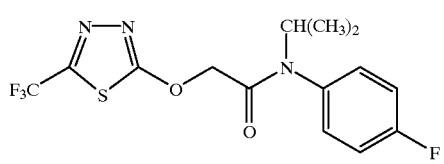

and at least one active compound of the formulae below
(b) glyphosate (N-phosphonomethyl-glycine) or its esters of the general formula (II)

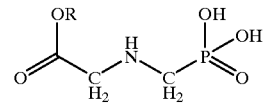

in which
R represents hydrogen or alkyl,
and/or salts formed by compounds of the general formula (II) with basic compounds
and/or
(c) glufosinate (2-amino-4-(hydroxy-methyl-phosphinyl)-butanoic acid), of the formula (III),

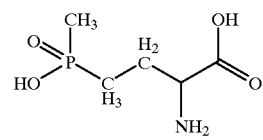

and/or salts formed by the compound of the formula (III) with basic compounds,
where 0.01 to 100 parts by weight of glyphosate and/or its salts or its esters and/or their salts, or of glufosinate and/or its salts, are used per part by weight of flufenacet.

In the general formula (I),
R preferably represents hydrogen, methyl, ethyl, n- or i-propyl or n-, i- or s-butyl.

Salts of compounds of the formulae (II) or (III) are preferably the sodium, potassium, ammonium, methylammonium, ethylammonium, n- or i-propylammonium, n-, i-, s- or t-butylammonium, dimethylammonium, diethylammonium, di—n-propyl-ammonium, di—i-propylammonium, di—n-butyl-ammonium, di—i-butylammonium, di—s-butylammonium, trimethylammonium, triethylammonium, tripropylammonium, tributylammonium, trimethylsulpho-nium and triethylsulphonium salts.

In the general formula (II),
R especially preferably represents hydrogen, methyl, ethyl or n- or i-propyl.

Especially preferred salts of compounds of the formulae (II) and (III) are the sodium, potassium, ammonium, methylammonium, ethylammonium, n- or i-propylammonium, dimethylammonium, diethylammonium, d—n-propylammonium, di—i-propylammonium and trimethylsulphonium salts.

The active compounds glyphosate (N-phosphonomethyl-glycine) and/or its sodium salt and/or its dimethylammonium salt and/or its i-propylammonium salt and/or its trimethylsulphonium salt (sulphosate) are very especially preferably emphasized as component (b) for the compositions according to the invention.

The active compounds glufosinate ((2-amino-4-(hydroxy-methyl-phosphinyl)-butanoic acid) and/or its ammonium salt are very especially preferably emphasized as component (c) for the compositions according to the invention.

Surprisingly, it has now been found that the above-described active compound combinations of (a) flufenacet (N-(4-fluoro-phenyl)-N-(i-propyl)-2-(5-trifluoromethyl-1,3, 4-thiadiazol-2-yl-oxy)-acetamide) and (b) glyphosate (N-phosphonomethyl-glycine) and/or its salts or its esters and/or their salts, or active compound combinations of (a) flufenacet (N-(4-fluoro-phenyl)-N-(i-propyl)-2-(5- trifluoromethyl-1,3,4-thiadiazol-2-yl-oxy)-acetamide) and (c) glufosinate and/or its salts show a particularly potent herbicidal activity and can be used successfully for efficiently controlling weeds.

Surprisingly, the herbicidal activity of the active compound combinations according to the invention of the active compound flufenacet and the active compound glyphosate and/or its salts or its esters and/or their salts considerably exceeds the total of the actions of the individual active compounds.

Again surprisingly, the herbicidal activity of the active compound combinations according to the invention of the active compound flufenacet and the active compound glufosinate and/or its salts considerably exceeds the total of the actions of the individual active compounds.

Thus, there exists a synergistic effect which could not have been predicted, and not only a complementation of action. The new active compound combinations are capable of effecting good control of weeds which are otherwise difficult to control (for example owing to resistance phenomena). The new active compound combinations thus represent a valuable enrichment in the field of weed control.

The active compound combinations according to the invention can be used, for example, in the case of the following plants:

dicotyledonous weeds of the genera

Cassia, Sinapis, Lepidium, Galium, Stellaria, Matricaria, Anthemis, Galinsoga, Chenopodium, Urtica, Senecio, Amaranthus, Portulaca, Xanthium, Convolvulus, lpomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Sphenoclea, Taraxacum.

monocotyledonous weeds of the genera

Echinochloa, Eriochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Dactyloctenium, Agrostis, Alopecurus, Apera, Aegilops, Phalaris.

Unless crop plants are resistant to the compounds of the formula (I) and/or (II) and/or (III), the active compound combinations according to the invention can also be employed for controlling weeds in these crop plants. Examples of crop plants which may be mentioned are:

monocotyledonous crops of the genera

Oryza, Zea, Triticum, Hordeum, Avena, Secale, Sorghum, Panicum, Saccharum, Ananas, Asparagus, Allium.

dicotyledonous crops of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Examples which may be mentioned of crop plants which show a certain degree of resistance to the active compound flufenacet are rice, maize, wheat, barley, oats, sugar cane, cotton, soya beans and oilseed rape.

Examples which may be mentioned of crop plants which are candidates for resistance to the active compound glyphosate and its salts or its esters and their salts and to the active compound glufosinate and its salts—in general generated by known recombinant methods—are maize, soya beans, cotton, sugar cane, oilseed rape and beet.

However, the use of the active compound combinations according to the invention is in no way restricted to these genera, but equally also extends to other plants.

The synergistic effect of the active compound combinations according to the invention is particularly pronounced at certain concentration ratios. However, the weight ratios of the active compounds in the active compound combinations can be varied within relatively wide ranges. In general, 0.01 to 100 parts by weight, preferably 0.05 to 50 parts by weight, and especially preferably 0.2 to 20 parts by weight, of active compound of the general formula (II) and/or (III) or salts thereof are used per part by weight of the active compound flufenacet.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are prepared in the known manner, for example by mixing the active compounds with extenders, that is to say liquid solvents and/or solid carriers, if appropriate using surfactants, that is to say emulsifiers and/or dispersants and/or foam formers.

If water is used as extender, it is also possible to use, for example, organic solvents as cosolvents. The following are mainly used as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

The following are suitable as solid carriers: for example ammonium salts and ground natural minerals such as kaolins, clays, talc, chalk, quartz, attapulgite, montmorillonite or diatomaceous earth, and ground synthetic minerals such as highly disperse silica, alumina and silicates; the following are suitable as solid carriers for granules: for example crushed and fractionated natural minerals such as calcite, marble, pumice, sepiolite, dolomite, and synthetic granules of inorganic and organic meals and granules of organic material such as sawdust, coconut shells, maize cobs and tobacco stalks; the following are suitable as emulsifiers and/or foam formers: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, and protein hydrolysates; the following are suitable as dispersants: for example lignin-sulphite waste liquors and methylcellulose.

Adhesives such as carboxymethylcellulose, natural and synthetic polymers in the form of powders, granules or latices such as gum arabic, polyvinyl alcohol, polyvinyl acetate, and natural phospholipids such as cephalins and lecithins and synthetic phospholipids can be used in the formulations. Other additives may be mineral and vegetable oils.

Colorants such as inorganic pigments, for example iron oxide, titanium oxide, Prussian Blue, and organic dyestuffs such as alizarin, azo and metal phthalocyanine dyes, and brace nutrients such as salts of iron, manganese, boron, copper, cobalt, molybdenum and zinc can be used.

In general, the formulations comprise between 0.1 and 95 percent by weight of active compound, preferably between 0.5 and 90%.

The active compound combinations according to the invention are generally applied in the form of ready mixes.

However, in the case of individual formulations, the active compounds included in the active compound combinations can also be mixed upon use, that is to say applied in the form of tank mixes.

The new active compound combinations, as such or in their formulations, can furthermore also be used as a mixture with other known herbicides, ready mixes or tank mixes again being possible. A mixture with other known active compounds such as fungicides, insecticides, acaricides, nematicides, bird repellants, growth substances, plant nutrients and soil conditioners is also possible. If appropriate, safeners may also be added. Furthermore, it may be advantageous for particular applications, in particular for the post-emergence method, to incorporate plant-tolerated mineral or vegetable oils (for example the commercial product "Oleo DuPont 11E") or ammonium salts such as, for example, ammonium sulphate or ammonium thiocyanate into the formulations as further additives.

The new active compound combinations can be applied as such, in the form of their formulations or the use forms prepared therefrom by further dilution, such as ready-to-use solutions, suspensions, emulsions, powders, pastes and granules. They are applied in the customary manner, for example by watering, spraying, atomizing, dusting or broadcasting.

The active compound combinations according to the invention can be applied mainly after the plants have emerged, that is to say by the post-emergence method.

The application rates of the active compound combinations according to the invention can be varied within a certain range; they depend, inter alia, on the weather and the soil factors. In general, the application rates are between 10 g and 10 kg per ha, preferably between 50 g and 5 kg per ha, especially preferably between 100 g and 2 kg per ha.

The good herbicidal action of the new active compound combinations can be seen from the examples which follow. While the individual active compounds show weaknesses with regard to the herbicidal action, the combinations always show a very good herbicidal action which exceeds a simple additive effect.

In herbicides, a synergistic effect is always present when the herbicidal action of the active compound combination exceeds that of the active compounds when applied individually.

The expected action for a given combination of two herbicides can be calculated as follows (cf. COLBY, S. R.: "Calculating synergistic and antagonistic responses of herbicide combinations", Weeds 15, pages 20–22, 1967):

If X=% damage by herbicide A (active ingredient of the formula I) at an application rate of p kg/ha and Y=% damage by herbicide B (active ingredient of the formula II) at an application rate of q kg/ha and E=the expected damage of herbicides A and B at application rates of p and q kg/ha, then $E=X+Y-(X*Y/100)$.

If the actual damage exceeds the calculated damage, the combination has a superadditive action, that is to say it has a synergistic effect.

It can be seen from the examples which follow that the herbicidal action found, on the weeds, of the active compound combinations according to the invention exceeds the calculated action, that is to say that the new active compound combinations have a synergistic effect.

USE EXAMPLES

Commercial formulations of the active compounds involved were used. The active compound concentrations required for the experiments were prepared by dilution with water.

Example A

Post-emergence test

Test plants which have a height of 5 to 15 cm are sprayed with the active compound preparation in such a way that the amounts of active compound desired in each case are applied per unit area. The concentration of the spray mixture is chosen in such a way that the amounts of active compound desired in each case are applied in 500 l water/ha.

After three weeks, the degree of damage to the plants is scored in % damage in comparison with the development of the untreated control.

The figures denote the following:

0%=no action (like untreated control)

100%=total destruction

Active compounds, application rates, test plants and results can be seen from the tables which follow, the -abbreviations used in the tables having the following meanings:

(I) flufenacet (N-(4fluoro-phenyl)-N-(i-propyl)-2-(5-trifluoromethyl-1,3,4-thiadiazol-2-yl-oxy)-acetamide)

(II-1) glyphosate-i-propylammonium (N-phosphonomethyl-glycine i-propyl-ammonium salt)

(III-1) glufosinate-ammonium (ammonium salt of 2-amino-4-(hydroxy-methyl-phosphinyl)-butanoic acid)

( ) If appropriate, the values calculated by the above Colby formula are shown in parentheses.

TABLE A1

Post-emergence test/greenhouse

| Active compound(s) | Application rate (g a.i./ha) | Apera spica-venti | Aloper-curus myosuroides | Echino-chloa crus-galli | Cheno-podium album |
|---|---|---|---|---|---|
| (I) | 60 | 60% | 60% | 60% | 0% |
| (II-1) | 30 | 0% | 0% | 0% | 0% |
| (I) + (II-1) | 60 + 30 | 90% (60%)* | 80% (60%)* | 70% (60%)* | 80% (0%)* |

TABLE A2

Post-emergence test/greenhouse

| Active compound(s) | Application rate (g a.i./ha) | Apera spica-venti | Aloper-curus myosuroides | Echino-chloa crus-galli | Cheno-Sinapis arvensis |
|---|---|---|---|---|---|
| (I) | 60 | 60% | 60% | 60% | 30% |
| (III-1) | 30 | 0% | 0% | 0% | 30% |
| (I) + (III-1) | 60 + 30 | 90% (60%)* | 80% (60%)* | 70% (60%)* | 70% (50%)* |

*expected value in accordance with Colby's formula

What is claimed is:

1. A composition comprising a synergistic combination of (a) flufenacet (N-(4-fluoro-phenyl)-N-(i-propyl)-2-(5-trifluoromethyl-1,3,4-thiadiazol-2-yl-oxy)-acetamide), of the formula (I),

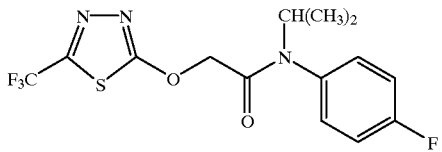
(I)

and at least one active compound of the formulae below
(b) glyphosate (N-phosphonomethyl-glycine) or its esters of the general formula (II)

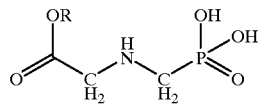
(II)

in which
R represents hydrogen or alkyl,
   and/or salts formed by compounds of the general formula (II) with basic compounds and/or
(c) glufosinate (2-amino4-(hydroxy-methyl-phosphinyl)-butanoic acid), of the formula (III),

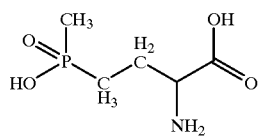
(III)

and/or salts formed by the compound of the formula (III) with basic compounds,
where 0.01 to 100 parts by weight of glyphosate and/or its salts or its esters and/or their salts, or of glufosinate and/or its salts, are used per part by weight of flufenacet.

2. A composition according to claim 1, characterized in that, in the general formula (II), R represents hydrogen, methyl, ethyl, n- or i-propyl or n-, i- or s-butyl.

3. A composition according to claim 1, characterized in that, in the general formula (II), R represents hydrogen, methyl, ethyl, n- or i-propyl.

4. A composition according to claim 1, characterized in that the salts formed with the basic compounds are in each case the sodium, potassium, ammonium, methylammonium, ethylammonium, n- or i-propyl ammonium, n-, i-, s- or t-butylammonium, dimethylammonium, diethyl ammonium, di—n-propylammonium, di—i-propylammonium, di—n-butyl ammonium, di—i-butylammonium, di—s-butylammonium, trimethylammonium, triethyl ammonium, tripropylammonium, tributylammonium, trimethylsulphonium or triethylsulphonium salts of the compounds of the general formulae (II) and/or (III).

5. A composition according to claim 1, characterized in that the salts formed with the basic compounds are in each case the sodium, potassium, ammonium, methylammonium, ethylammonium, n- or i-propylammonium, dimethylammonium, diethylammonium, di—n-propylammonium, di—i-propylammonium and trimethylsulphonium salts of the compounds of the general formulae (II) and/or (III).

6. A composition according to claim 1, characterized in that component (b) is the active compound glyphosate (N-phosphonomethyl-glycine) and/or its sodium salt and/or its dimethylammonium salt and/or its i-propylammonium salt and/or its trimethylsulphonium salt (sulphosate).

7. A composition according to claim 1, characterized in that component (c) is the active compound glufosinate ((2-amino-4-(hydroxy-methyl-phosphinyl)-butanoic acid) and/or its ammonium salt.

8. A method of controlling weeds, comprising applying a composition according to claim 1 on to undesired plants and/or their environment.

9. A process for the preparation of a herbicidal composition comprising mixing a composition according to claim 1 with surfactants and/or extenders.

* * * * *